United States Patent [19]
Kissel et al.

[11] Patent Number: 5,364,628
[45] Date of Patent: Nov. 15, 1994

[54] PHARMACEUTICAL COMPOSITIONS

[75] Inventors: Thomas Kissel, Ehrenkirchen, Germany; Henriette Schrank, Riehen, Switzerland; Hans-Rainer Hoffmann, Neuwied, Germany

[73] Assignees: Sandoz Ltd., Basel, Switzerland; LTS Lohmann Therapie-Systeme GmbH & Co., Neuwied, Germany

[21] Appl. No.: 141,832

[22] Filed: Oct. 22, 1993

Related U.S. Application Data

[63] Continuation of Ser. No. 804,630, Dec. 9, 1991, abandoned, which is a continuation of Ser. No. 597,470, Oct. 3, 1990, abandoned, which is a continuation of Ser. No. 298,457, Jan. 18, 1989, abandoned, which is a continuation of Ser. No. 96,571, Sep. 3, 1987, abandoned, which is a continuation of Ser. No. 740,917, May 31, 1985, abandoned.

[51] Int. Cl.$^5$ .............................................. A61F 13/02
[52] U.S. Cl. ...................................... 424/448; 424/449
[58] Field of Search ............................... 424/448, 449

[56] References Cited

U.S. PATENT DOCUMENTS

| | | | |
|---|---|---|---|
| 3,598,122 | 8/1971 | Zafaroni | 424/448 |
| 3,641,237 | 2/1972 | Gould et al. | 424/16 |
| 4,078,568 | 3/1978 | Etes | 424/448 |
| 4,136,145 | 1/1979 | Fuchs | 264/164 |
| 4,136,162 | 1/1979 | Fuchs | 424/443 |
| 4,409,206 | 10/1983 | Stricker | 424/444 |
| 4,608,249 | 8/1986 | Otsuka | 424/448 |
| 4,694,464 | 9/1987 | Alderman | 424/448 |
| 4,755,384 | 7/1988 | Mallasz | 424/448 |
| 4,806,341 | 2/1989 | Chien | 424/448 |
| 4,834,978 | 5/1989 | Nuwayser | 424/448 |

FOREIGN PATENT DOCUMENTS

| | | |
|---|---|---|
| 0013606 | 7/1980 | European Pat. Off. . |
| 0072251 | 2/1983 | European Pat. Off. . |
| 2514642 | 4/1983 | France . |
| 2005084 | 8/1970 | Germany . |
| 2913752 | 12/1979 | Germany . |
| 3204551 | 8/1983 | Germany . |
| 0206519 | 12/1983 | Japan . |
| 0025320 | 2/1984 | Japan . |
| 2098865 | 12/1982 | United Kingdom . |
| 8300092 | 1/1983 | WIPO . |

OTHER PUBLICATIONS

Derwent 84014240 1983.
Derwent 84071329 1984.
Derwent 84104847 1984.
Derwent 84021059 1983.
Derwent 83741952 1983.
Derwent 84148575 1984.
Derwent 40807U 1973.
Derwent 84133853 1984.
Derwent 72524 1982.
Derwent 71521T 1972.
Derwent 87537V 1974.
Derwent 66312C 1980.
Derwent 72017T 1972.
Derwent 73601D 1981.
Derwent 75592D 1981.
Chemical Abstracts No. 97:156157 1982.

Primary Examiner—Gabrielle Phelan
Attorney, Agent, or Firm—Robert S. Honor; Melvyn M. Kassenoff; Carl W. Battle

[57] ABSTRACT

The present invention provides a pharmaceutical composition for the transdermal systemic administration of an active agent characterized in that the active agent is bopindolol or methysergide. Also the present invention provides a pharmaceutical composition for the transdermal systemic administration of a pharmacologically active agent characterized in that it contains bopindolol, tizanidine, clemastine, ketotifen or methysergide as active agent in a reservoir comprising a hydrophilic polymer. Furthermore a pharmaceutical composition for the transdermal systemic administration of pharmacologically active agents characterised in that the pharmacologically active agent is in a reservoir comprising a polyacrylate polymer containing cationic ester groups.

8 Claims, 1 Drawing Sheet

PHARMACEUTICAL COMPOSITIONS

This is a continuation of application Ser. No. 07/804,630, filed Dec. 9, 1991, now abandoned, which in turn is a continuation of application Ser. No. 07/597,470, filed Oct. 3, 1990, now abandoned, which in turn is a continuation of application Ser. No. 07/298,457, now abandoned, filed Jan. 18, 1989, which in turn is a continuation of application Ser. No. 07/096,571, now abandoned, filed Sep. 3, 1987, which in turn is a continuation of application Ser. No. 06/740,917, filed May 31, 1985, which is now abandoned.

This invention relates to pharmaceutical compositions, especially for the systemic transdermal administration of pharmacologically active agents.

Many pharmaceutical compositions have been proposed for the sustained transdermal administration of pharmacologically active agents into the systemic circulation. These generally comprise essentially a solid reservoir or matrix made of a solid polymer or gel containing the pharmacologically active agent dispersed throughout. On one side of the drug reservoir there is a backing member impermeable to the drug and on the other side a protective peel strip which is taken off before use. The backing member may be larger than the drug reservoir and may carry near its edges an adhesive layer to retain the protective peel strip and, when this is removed, to stick the unit to the skin. Additionally or alternatively a drug-permeable adhesive layer may be provided on the reservoir to retain the protective peel strip and stick the unit to the skin. In some proposals the drug reservoir has attached to it a drug-permeable control membrane or member, through which the pharmacologically active agent passes, in order to regulate the rate of passage of the active agent, e.g. to prevent dose dumping.

In use after the peel strip has been removed, the unit is stuck into the skin and the pharmacologically active agent passes from the drug reservoir to the skin. More complicated systems have been proposed to improve the penetration rate of the pharmacologically active agent through the skin. However, most systems do not provide a sufficient penetration rate of the pharmacologically active agent or suffer from other disadvantages. Before the priority date of the present application the transdermal pharmaceutical compositions for systemic administration of drugs commercially available on a wide scale were restricted to pharmacologically active agents which exist in liquid form e.g. scopolamine or nitroglycerin, and which in any event easily penetrate the skin.

There is thus a need for new approaches to the transdermal application of solid and liquid pharmacologically active agents using controlled release systems.

We have now surprisingly found that the pharmacologically active agent bopindolol, 4-(2-benzoyloxy-3-tert-butylaminopropoxy)-2-methylindole, a beta-blocker which is known for oral administration e.g. for the treatment of hypertension, and methysergide (9,10-didehydro-N-[1-(hydroxymethyl)propyl]-1,6-dimethylergoline-8-carboxamide, a known serotonin antagonist e.g. for the prophylaxis of migraine, have especially interesting properties for transdermal administration. These are hereinafter referred to as the active agents of the invention.

The penetration of these active agents through the skin may be observed in standard in vitro or in vivo tests.

One in vitro test is the well known diffusion test which may be effected according to the principles set out in GB 2098865 A and by T. J. Franz in J. Invest. Dermatol (1975) 64, 194–195. Solutions containing the active agent in unlabelled or radioactively labelled form are applied to one side of isolated pieces of intact human skin or hairless rat skin about 2 cm$^2$ in area. The other side of the skin is in contact with physiological saline. The amount of active agent in the saline is measured in conventional manner, e.g. by HPLC or spectrophotometric techniques, or by determining the radioactivity.

Typically using rat skin a penetration flux of from 0.1 to 10 microgram/cm$^2$/hour over 24 hours is observed for the active agents.

In one aspect the present invention provides a method of systemically administering the active agent bopindolol or methysergide which comprises administering the active agent to the skin. In a further aspect the present invention provides the use of bopindolol or methysergide as active agent in the manufacture of a medicament suitable for systemic transdermal administration. In a further aspect the present invention provides a pharmaceutical composition for the transdermal systemic administration of an active agent characterised in that the active agent is bopindolol or methysergide.

In general for application e.g. behind the ear an amount of bopindolol or methysergide from about 1 to 6 mg is indicated, e.g. 5 mg for a dose for 1 to 3 days.

The active agents of the invention may be administered in any conventional liquid or solid transdermal pharmaceutical composition, e.g. as described in Remington's Pharmaceutical Sciences 16th Edition Mack; Sucker, Fuchs and Spieser, Pharmaceutische Technologie 1st Edition, Springer and in GB 2098865 A or DOS 321205 the contents of which are incorporated herein by reference. Conveniently the composition is in the form of a viscous liquid, ointment or solid matrix. The active agent may be incorporated in a plaster.

We have now found that the above active agents, bopindolol and methysergide, as well as the following pharmacologically active agents tizanidine, ketotifen and clemastine may be advantageously administered transdermally from a drug reservoir comprising a hydrophilic polymer having the pharmacologically active agent dispersed throughout.

Tizanidine, ketotifen and clemastine have previously been disclosed for transdermal administration. GB 2098865 A discloses topical microemulsions containing these pharmacologically active agents. The microemulsions are to be applied to the skin as a cream.

Tizanidine is a known myotonolytic agent e.g. for the treatment of local muscle spasms e.g. rheumatic-pains and spastic conditions. Ketotifen and clemastine are anti-histamines e.g. for the treatment of allergic conditions. Ketotifen also is an anti-anaphylatic agent, e.g. for the prophylaxis of asthma.

In a further aspect the present invention provides a pharmaceutical composition for the transdermal systemic administration of pharmacologically active agents characterised in that it contains bopindolol, tizanidine, clemastine, ketotifen or methysergide in a reservoir comprising a hydrophilic polymer. In yet a further aspect the present invention provides the use of these active agents in a hydrophilic polymer for the manufacture of a transdermal medicament suitable for systemic administration of the active agent through intact skin.

The hydrophilic polymers take up water and are permeable to water, e.g. moisture from the skin, although the polymers may be insoluble in water. The polymers may swell and provide release of a large amount of pharmacologically active agent leading to a high concentration gradient of pharmacologically active agent between the skin surface and stratum corneum at a pH of from 4 to 7, preferably at skin pH, e.g. 5.5. If desired they may be soluble in organic solvents. Examples of suitable polymers include polyacrylamide and its co-polymers, polyvinylpyrrolidone (PVP), vinyl acetate/vinyl alcohol co-polymers, polyvinyl alcohol (PVA) and derivatives, ethyl cellulose and other cellulose and starch derivatives.

The polymer preferably has a mean molecular weight of from about 50,000 to about 300,000 Daltons, such as 100,000 to 200,000 Daltons, and is preferably film forming.

Hydrophilic polyacrylates are preferred polymers. The acrylate may be substituted, e.g. a methacrylate. They may be commercially available acrylate/methacrylate co-polymers. Some or all of the acid groups may be esterified, e.g. with alkyl groups such as methyl or ethyl groups. Preferably at least 2% of the alkyl groups may contain polar substituents, e.g. a hydroxy group.

It has been found that polyacrylates containing cationic functional groups are especially preferred.

Transdermal pharmaceutical compositions for the systemic administration of pharmacologically active agents through intact skin wherein the active agent is in a reservoir comprising a polyacrylate containing cationic functional groups are novel and form part of the present invention.

The present invention also provides the use of a pharmacologically active agent in a polyacrylate containing cationic groups for the manufacture of a medicament suitable for transdermal systemic administration of the pharmacologically active agent through intact skin of a subject. In another aspect the present invention provides a method of systemically administering a pharmacologically active agent to a subject which comprises contacting a reservoir of the pharmacologically active agent in a polyacrylate containing cationic ester groups to intact skin.

Examples of cationic groups include dialkylaminoalkyl groups, e.g. dimethylaminoalkyl groups.

Especially preferred cationic groups include quaternary ammonium groups, preferably a tri(alkyl)aminoalkyl group. Examples of such groups are trimethylaminoethyl ester groups.

The polyacrylate may contain some carboxylic acid groups in free form or salt anions, e.g. chloride anions in order to balance the cationic groups.

The ratio of cationic groups to neutral groups is preferably from 1:10 to 1:50 e.g. from 1:20 to 1:40.

Preferably the polymers have an alkali count (defined in analogous manner to acid count of from about 10 to about 200 mg KOH per gram polymer, e.g. 10 to 30 mg KOH per gram polymer.

Examples of commercially available polymers of this type include:

1) Polymers of acrylate and methacrylate esters containing methyl and ethyl neutral ester groups and trimethylaminoethyl cationic ester groups. Chloride ions are present. Mean Molecular weight 150000 Daltons. Viscosity (20° C.), maximum 15 cP. Refractive index 1.380–1.385. Density 0.815–0.835 g/cm$^3$. Ratio of cationic ester groups to neutral alkyl groups 1:20 giving an alkali count of 28.1 mg KOH per gram polymer (Eudragit RL 100 Registered Trade Mark available from Röhm, Darmstadt, W.Germany) or 1:40 giving an alkali count of 15.2 mg KOH per gram polymer (Eudragit RS 100 Registered Trade Mark, also available from Röhm).

2) Polymer of methacrylate esters containing trimethylaminoethyl cationic ester groups and other neutral ($C_{1-4}$)alkyl ester groups. Chloride ions are present. Mean molecular weight 150,000. Viscosity (20° C.) 10 cP. Refractive Index 1.38. Density 0.815. Alkali number of 180 mg KOH per gram polymer (Eudragit E 100, Registered Trade Mark, also available from Röhm).

The drug reservoir may contain plasticizers and/or softeners preferably skin compatible tensides e.g. to provide flexibility to the unit, and/or to dissolve partially or totally the pharmacologically active agent in the reservoir.

Examples of additives include:

1) Polyoxyethylene fatty alcohol ethers. The alcohol may e.g. be a $C_{12-18}$ alcohol. The HLB value may be e.g. from 10 to 18. A preferred example is polyoxyethylene-(10) oleyl ether. A suitable ether may have a viscosity (25° C.) of about 100 cP, a solidification point of about 16° C., an HLB value of 12.4 and an acid count maximum 1.0 (Brij 97 Registered Trade Mark available from Atlas Chemie W.Germany).

2) Polyoxyethylene Sorbitan fatty acid esters. The fatty acid may be e.g. a $C_{12-18}$ fatty acid. The HLB value may be e.g. from 10 to 18. A preferred example is polyoxyethylene-(20) sorbitan monooleate, e.g. Tween 80, Registered Trade Mark available from Atlas Chemie, W.Germany.

3) Polyoxyethylene-(5–40) stearic acid esters, e.g. Myrj (Registered Trade Mark) available from Atlas Chemie, W.Germany.

4) Polyoxyethylene glycol fatty alcohol ethers, e.g. polyethylene glycol-(6–25) cetyl ether, glycerin polyethylene ricinoleate, glycerin polyethylene glycol stearate (Cremophor brand, Registered Trade Mark available from BASF W.Germany).

5) Polyoxyethylene glycols of MW from 200 to 600 Daltons, e.g. 300 or 400 Daltons.

6) Esters of poly(2–7)ethylene glycol glycerol ether having at least one hydroxyl group and an aliphatic ($C_{6-22}$) carboxylic acid, e.g. Polyethylene glycol-(7) glyceryl cocoate, e.g. Cetiol HE, Registered Trade Mark, from Henkel, W.Germany.

7) Adipic acid lower alkyl esters, e.g. di-n-butyl adipate and diisopropyl adipate.

8) Glycerin polyethylene glycol ricinoleate e.g. Product of 35 moles ethylene oxide and castor oil e.g. Brand Chremophor EL Registered Trade Mark, obtainable from BASF, W.Germany.

9) Triacetin-(1,2,3).

The amount and type of additive required will depend on a number of factors, e.g. the HLB value of the tenside and the flexibility of the unit required. Surprisingly the amount of additive does not significantly influence the capability of the polyacrylate to form films. Generally the weight ratio of tenside to the hydrophilic polymer is from about 1:10 to 5:1, e.g. 1:10 to 1:3.

The drug reservoir may contain skin penetration promoters, e.g. 1-dodecyl azacyc loheptan-2-one(azone) and N,N-diethyl-m-toluamide (DEET).

The amount and type of skin penetration promoter, and/or additives present will depend on a number of factors. Generally the weight ratio of skin penetration promoting agent to hydrophilic polymer will be from about 1:1 to 1:10. Preferably the amount of tenside and/or skin penetration promoter is from about 3 to about 50%, preferably 20 to 40% by weight of the pharmaceutical composition.

If desired the drug reservoir may contain a hydrophobic elastomer, e.g. a synthetic resin. Such resins are conventional in the plaster art. Suitable resins include non-swellable acrylate resins. These may if desired be adhesive. The weight ratio of hydrophilic polymer to resin may for example be from 1:0.5 to 1:10. The resin may contain modifiers, extenders, e.g. of softening point about 50° to 100° C. Such extenders may have adhesive or softening properties. Examples of such extenders include resin acids, glyceryl and phthalate esters of resin acids, hydrogenated abietyl alcohol and its phthalate esters. The extenders for example be present in an amount of from 5 to 40% of the weight of the resin.

Any pharmacologically active agent capable of penetration of the skin may be dispersed throughout the hydrophilic polymer. The indication for which the active agent is used is not critical. It is preferred that the daily transdermal dose for such agents is less than 20 mg per day, e.g. less than 10 mg per day.

The active agent for use in any of the pharmaceutical compositions mentioned above may be in free form e.g. free base form or in pharmaceutically acceptable salt form e.g. pharmaceutically acceptable acid addition salt form.

Such acid addition salt forms include the hydrogen malonate, hydrogen maleate, hydrogen fumarate, hydrochloride, tartrate etc. Preferably a solid active agent has an average particle diameter of from about 30 to about 50 microns.

The active agent may be partly suspended and/or partly dissolved in the reservoir. It may be dispersed so finely that to the eye a smooth homogenous film results.

The pharmaceutical compositions of the invention are useful for the systemic administration of pharmacologically active agents through intact skin, as indicated in standard in vitro and in vivo tests.

The release of active agent from the pharmaceutical compositions may be followed for example by determining e.g. by ultraviolet spectroscopy, the amount of active agent released on shaking the pharmaceutical composition in 0.9% NaCl solution at 37° C. at a paddle speed of about 120 rpm.

The penetration of the active agent through isolated rat and human skin may be followed in the well known diffusion test effected according to the principles, e.g. set out in GB 2098865 A and in T. J. Franz, J. Invest. Dermatol (1975), 64, 191–195. The pharmaceutical compositions of the invention are applied to the external side of isolated rat or human skin pieces about 2 cm$^2$ in area. The rat skin is hairless. The other side is continuously washed with physiological saline. The amount of active agent in the saline is determined in conventional manner, e.g. HPLC. The penetration flux over 24 hours may then be ascertained, and if desired the steady state flux. The penetration flux rate is in the order of 1 to 10 micrograms/cm$^2$/hour.

Alternatively the penetration of the active agent may be followed in vivo by applying the pharmaceutical composition to intact skin, e.g. on the chest, back, arm or behind the ear, of a subject and measuring the amount of active agent in the blood.

The pharmaceutical compositions of the invention may be used for the same indications as known for oral or intravenous administration. The amount of pharmaceutically active agent to be administered will individually depend on the drug release characteristics of the pharmaceutical compositions, the drug penetration rate observed in in vitro and in vivo tests, the potency of active agent, the size of the skin contact area, the part of the body to which the unit is stuck, and the duration of action required. The amount of active agent and area of the pharmaceutical composition etc. may be determined by routine bioavailability tests comparing the blood levels of active agents after administration of the active agent in a pharmaceutical composition according to the invention to intact skin and blood levels of active agent observed after oral or intravenous administration of a therapeutically effective dose of the pharmacologically active agent.

Given the daily dose of a drug for oral administration, the choice of a suitable quantity of drug to be incorporated in a transdermal composition according to the invention will depend upon the pharmacokinetic properties of the active agent, including the first pass effect; the amount of drug which can be absorbed through the skin from the matrix in question for a given area of application and in a given time; and the time for which the composition is to be applied. Thus, a drug with a high first pass effect may require a relatively low quantity in the transdermal composition when compared with the oral daily dose, since the first pass effect will be avoided. On the other hand, generally a maximum of only approx. 50% of the drug in the matrix is released through the skin in a 3 day period.

The pharmaceutical compositions of the invention in general have for example an effective contact area of drug reservoir on the skin of from about 1 to about 50 square centimetres, preferably about 2 to 20 square centimetres, and are intended to be applied for from 1–7 days, preferably 1–3 days.

Examples of representative doses are:
1) Tizanidine
   A dose of 20 mg in a patch of ca 10 cm$^2$ to be administered once every 3 days for the systemic treatment of rheumatic pains and muscle spasms.
2) Bopindolol
   A dose of 1 to 10 mg in a patch of 10 cm$^2$ to be administered once over 3 consecutive days in each week for treatment of hypertension.
3) Clemastine
   A dose of about 1 to 20 mg in a patch of ca 10 cm$^2$ to be administered once every 3 days for treatment of allergies, eg. hay fever.
4) Ketotifen
   A dose of about 1 to 20 mg in a patch of ca 10 cm$^2$ to be administered once every 3 days for prophylaxis of asthma.
5) Methysergide
   A dose of about 1 to 10 mg in a patch of ca 10 cm$^2$ to be administered once every 3 days for prophylaxis of migraine and migraine interval treatment.

The pharmaceutical compositions of the invention may be produced in conventional manner by dispersing or dissolving an appropriate pharmacologically active agent through a hydrophilic drug reservoir. The weight ratio of pharmacologically active agent to hydrophilic polymer may vary between wide limits. The weight ratio may be for example sufficient to produce a supersaturation of the pharmacologically active agent in the drug reservoir. In general the weight ratio is from about 1:10 to about 1:1.

For example in the case of tizanidine the amount may be for example from 10 to 40 percent, e.g. 15 to 30 or 20 to 25 percent, by weight.

If the drug reservoir is not itself adhesive a pressure sensitive adhesive may be used to stick the drug reservoir to intact skin. Any conventional adhesive may be used, e.g. a polyacrylate. The layer may be applied to the drug reservoir and have a thickness of from about 1 to about 200 microns preferably 10 to 100 microns. If the adhesive layer is thin enough then the pharmacological agent will pass through it. Alternatively the adhesive layer may be applied to the edges of an outer cover for the drug reservoir and the outer cover stuck to the intact skin holding the drug reservoir in close contact with the intact skin.

The drug reservoir may be produced in conventional manner, e.g. in an adhesive plaster or patch. If it is a polymer matrix it may be produced by dispersing or dissolving the pharmacologically active agent in a solution of the polymer and other additives in a volatile organic solvent, e.g. ethanol, methylene chloride, or acetone. A film is formed by spreading the dispersion or solution over the outer protective cover. The wet film may have a thickness of about 0.05 to 0.5 millimetres, e.g. 0.1 to about 0.3 millimetres. The film is allowed to dry, e.g. at room temperature or a slightly elevated temperature below 50° C. The drug reservoir may be built up in a series of layers and then any adhesive layer provided in the last layer. The pharmaceutical compositions of the invention may be produced in conventional manner for skin penetration pharmaceutical compositions.

BRIEF DESCRIPTION OF THE DRAWINGS

In FIG. 1 and 2 there are several layers a-d and in the case of FIG. 2, additionally layer e. Layer a is a medical cover made out of e.g. polyester/aluminium laminate foil. Layer b is an occulsive foil, e.g. of aluminium foil. If desired this may be omitted. Layer c may be made out of 1 to 10 layers of a drug reservoir. The drug reservoir is a homogenous dispersion of active agent particles or a solution of active agent in a polymer matrix. Layer d may be an adhesive layer. In one embodiment (not shown) the layer d may extend to between the outer edges of layer a and layer e. Alternatively the layer e may be omitted completely. Layer a may extend around layers b to d in FIG. 2. Layer e is a protective peel off layer which is stuck to the adhesive layer as well as to the edges of the cover layer a.

Figure 1:
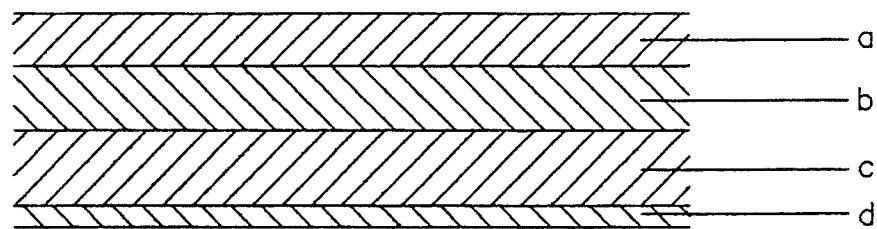
FIG. 1 of the accompanying drawings gives a schematic cross-section through the layers of a representative pharmaceutical composition according to the invention.
Figure 2:
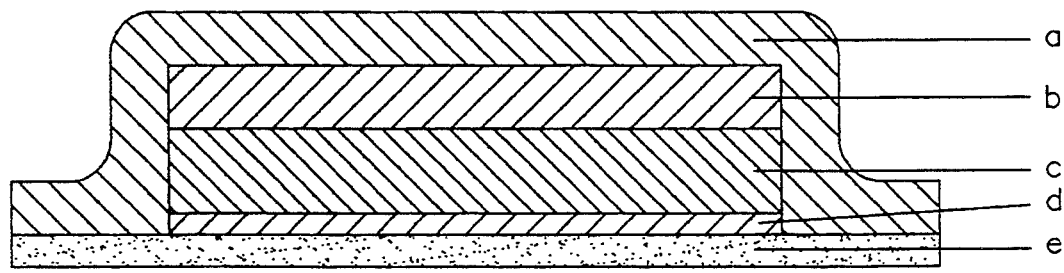
FIG. 2 of the accompanying drawings gives a schematic cross-section of a another embodiment, e.g. in the form of a bandage or plaster.

On use any protective layer e is peeled off and the unit stuck to intact skin.

In the following examples all temperatures are in degrees Centigrade and are uncorrected. All amounts are in parts by weight unless otherwise stated.

Details of components are given in Lexicon for Pharmazie, Kosmetic and angrenzende Gebiete by H. P. Fiedler, 2 Edition, Cantor Aulendorf, W.Germany or from the relevant manufacturers.

In the following examples, the indicated terms have the meaning shown below:

PAM Amine polymer RL: Polyacrylate/methacrylate cationic polymer as defined above under the term EUDRAGIT RL 100.

PAM Amine polymer RS: Polyacrylate/methacrylate cationic polymer as defined above under the term EUDRAGIT RS 100.

PAM Amine polymer E: Polymethacrylate cationic polymer as defined above under the term EUDRAGIT E 100.

Polyoxyethylene(10) oleyl ether: BRIJ 97 as derived above. Glycerin Polyethylene glycol(35) (ricinoleate=Cremophor EL as defined above.)

Polyoxyethylene(20) sorbitan monooleate=Tween 80 as defined above.

Polyethylene(7) glycol glyceryl cocoate=Cetiol HE as defined above. Acrylate synthetic resin is self cross-linking acrylate Brand Durotack 280–2416 available from Delft National Chemie Zutphen Netherlands available as a light yellow solution containing as solvent 57% ethyl acetate, 32% ethanol, 9% hexane, 2% methanol: solids content 41%, Viscosity (Brookfield)=2100–6000 mPas, Plasticity (Williams)±3 mm, Density 0.94 Flashpoint 0.94.

EXAMPLE A

Preparation of pharmaceutical composition containing a hydrophilic polymer

Composition

Pharmacologically active agent 20%

Hydrophilic polymer 40%

Tenside 40%

1.2 g of hydrophilic polymer are dissolved in 3 g acetone or ethanol or other appropriate volatile organic solvent with stirring in 1 to 2 hours. 0.6 g pharmacologically active agent and 1.2 g of tenside softener are added. The mixture is vigorously stirred for about 5 to 20 minutes with a high speed stirrer to give a viscous mass.

The mass is spread as a film on top of an aluminised polyester foil (thickness 23 microns) using a conventional apparatus, e.g. an Erichsen film apparatus Model 411/150. The mass is spread across the foil at a speed of 18 mm/sec to produce a film of thickness 0.2 mm when wet.

The film is allowed to dry at room temperature over 4 to 6 hours. The resultant hydrophilic polymer drug matrix weighs 8.5 mg per square centimetre and contains 1.7 mg active agent per square centimetre.

A further film of an acrylate adhesive (Rohm Pharma 7708/47) is then applied onto the drug polymer matrix as a thin layer (0.1 mm thickness) in analogous manner.

The aluminium foil is then cut up into patches about 10 sq cm in area.

Unless otherwise stated the drug matrix is built up from one film layer. It may if desired be built up as more than one layer.

The release of active agent is measured in vitro in standard skin diffusion tests through freshly isolated hairless rat skin. The rat skin piece is located in a Franz diffusion chamber—see T. J. Franz, J. Invest. Dermatol 1975 (64) 191–195. The receptor phase is pumped continuously and every hour samples are taken and measured for active agent content using HPLC. The trial lasts 24 hours and the penetration flux over 24 hours (hereinafter referred to as "flux") and if desired a steady state flux after a lag time of 3 to 10 hours is measured.

EXAMPLE 1

Tizanidine composition
Prepared as disclosed in Example A with a composition of
  Tizanidine hydrochloride 20%
  PAM Amine Polymer RL 40%
  Polyoxyethylene-10 oleyl ether 40%
  Active agent penetration rate in rat skin:
  Penetration Flux± =0.0145 mg/cm$^2$/hr
  Total penetration± =0.290 mg/cm$^2$ ca 21.46%
  Remainder detected in plaster ca 47%

EXAMPLE 2

Tizanidine composition
Prepared in analogous manner to that described in Example A with a composition of
  Tizanidine hydrochloride 1.144 g
  PAM Amine polymer RL 1.928 g
  Polyoxyethylene-10 oleyl ether 1.928 g
  The active agent is dissolved in 5 g ethanol as solvent.
  Spreading speed 6 mm/sec.
  Thickness of wet film 0.25 mm.
  Concentration of active agent in film 2.6 mg/cm$^2$
  No adhesive acrylate film is present.
  Active agent penetration rate through rat skin:
  Penetration Flux=8.5 microgram/cm$^2$/hr
  Steady state flux=16.2 microgram/cm$^2$/hr
  In a clinical trial a 2 cm$^2$ patch of the composition is applied to the left underarm and after 12, 24 and 36 hours the remaining tizanidine content in the patch determined.
  Flux rate=5.1 microgram/cm$^2$/hr

EXAMPLE 3

Prepared as described in Example 2 using as solvent methylene chloride instead of ethanol. Composition:
  Tizanidine hydrochloride 1.144 g
  PAM Amine polymer RL 1.928 g
  Polyoxyethylene-10 oleyl ether 1.628 g
  Triacetin (1,2,3) 0.250 g
  Penetration rate through rat skin:
  Penetration Flux 10.4 microgram/cm$^2$/hr
  In a clinical trial a 2 cm$^2$ patch was applied as in Example 2.
  Penetration Flux 4.9 microgram/cm$^2$/hr

EXAMPLE 4

Tizanidine Pharmaceutical Composition
Prepared in analogous manner to that disclosed in Example 2.
  Spreading speed=18 mm/sec
  Thickness of wet film: 0.2 mm
  Concentration of active agent: 1.7 mg/cm$^2$
  An acrylate film adhesive layer is applied as in Example A.
  Penetration rate through rat skin.
  Penetration Flux=14.5 microgram/cm$^2$/hr
  Steady state Flux=30.8 microgram/cm$^2$/hr

EXAMPLE 5

Tizanidine pharmaceutical compositions
The tenside in Example 2 is replaced by an equivalent mount of
  i) Polyethylene glycol 300
  ii Glycerin polyethylene glycol-(35) ricinoleate
  iii) Polyoxyethylene-(20) sorbitan monooleate
  iv) azone
  and/or
  PAM Amine polymer RL is replaced by PAM Amine polymer RS or
  PM Amine polymer E.

EXAMPLES 6–8

Clemastine Pharmaceutical Compositions
The following compositions are made in analogous manner to example 2.

| Example | 6 | 7 | 8 |
| --- | --- | --- | --- |
| Clemastine hydrogen fumarate | 1 g | 1.34 g | 1 g |
| PAM Amine polymer RL | 2 g | — | — |
| PM Amine polymer E | — g | 2.41 g | 2.66 g |
| Polyoxyethylene (10) oleyl ether | 2 g | 1.25 g | — |
| Polyethylene glycol 300 | — | — | 1.34 g |
| Solvent | Acetone | Acetone | CH$_3$OH |
| Solvent amount (g/g dry film) | 0.6 | 0.5 | 2.0 |
| Thickness of wet film (mm) | 0.2 | 0.15 | 0.3 |
| Spreading speed (mm/sec) | 6 | 6 | 6 |
| Acrylate adhesive film (Wet film thickness) | 0.15 | None | None |
| Active Agent Penetration through isolated rat skin. | | | |
| Penetration Flux (microgram/cm$^2$/hr) | 1.3 | 4.5 | 3.2 |
| Steady state flux (microgram/cm$^2$/hr) | 10 | 12 | 8.6 |

EXAMPLES 9–12

Bopindolol pharmaceutical compositions
The following compositions are made in analogous manner to Example 2.

| Example | 9 | 10 | 11 | 12 |
| --- | --- | --- | --- | --- |
| Bopindolol hydrogen malonate | 1.275 g | 1.275 g | — | — |
| Bopindolol free base | — | — | 1.0 g | 1.0 g |
| PAM Amine polymer RL | 1.225 g | 1.225 g | — | — |
| PM Amine polymer E | — | — | 2.665 g | 2.665 g |
| Polyoxyethylene-(10) oleyl ether | — | 0.25 g | 1.335 g | — |
| Polyethylene-(9) glycol glyceryl cocoate | — | — | — | 1.335 g |
| Azone | 2.5 g | 2.25 g | — | — |
| Solvent | CH$_2$Cl$_2$ | CH$_2$Cl$_2$ | CH$_3$OH | CH$_3$OH |
| Solvent amount (g/g dry film) | 1.0 | 1.0 | 4.0 | 4.0 |
| Thickness of wet film (mm) | 0.25 | 0.25 | 0.3 | 0.3 |
| Spreading speed (mm/sec) | 6 | 6 | 6 | 6 |
| Acrylate adhesive film | None | None | None | None |

-continued

| Example | 9 | 10 | 11 | 12 |
|---|---|---|---|---|
| (Wet film thickness) Active Agent Penetration through isolated rat skin. | | | | |
| Penetration Flux (microgram/cm$^2$/hr) | 1.7 | 4.0 | 11.1 | 8.6 |
| Steady Rate flux (microgram/cm$^2$/hr) | 5.7 | 12.5 | 59.0 | 33.0 |

EXAMPLES 13–16

Ketotifen pharmaceutical compositions

The following compositions are made in analogous manner to Example 2.

| Example | 13 | 14 | 15 | 16 |
|---|---|---|---|---|
| Ketotifen hydrogen fumarate | 0.5 g | 0.5 g | — | — |
| Ketotifen free base | — | — | 1.0 g | 1.0 g |
| PAM Amine Polymer RL | — | — | 2.0 g | 2.0 g |
| PM Amine Polymer E | 2.5 g | 2.5 g | — | — |
| Polyoxyethylene (20) sorbitan monooleate | — | — | — | 2.0 g |
| Polyethylene glycol 300 | — | 2.0 g | — | — |
| Polyethylene glycol-(7) glyceryl cocoate | 2.0 g | — | 2.0 g | — |
| Solvent | Acetone | Acetone | Acetone | Acetone |
| Thickness of wet film (mm) | 0.2 | 0.2 | 0.2 | 0.2 |
| Spreading speed (mm/sec) | 6 | 6 | 6 | 6 |
| Acrylate adhesive film | None | None | None | None |
| Active Agent Penetration through isolated rat skin Penetration Flux (microgram/cm$^2$/hr) | 6.8 | 8.5 | 4.0 | 2.8 |
| Steady state flux (microgram/cm$^2$/hr) | 10.0 | 15.0 | 18.0 | 12.0 |

EXAMPLE B

In analogous manner to that described in Example A a pharmaceutical composition is made without an acrylate adhesive layer. The drug matrix is based on an elastomer.

| | B1 | B2 |
|---|---|---|
| Weight g/m$^2$ | 80 | 79 |
| Tizanidine hydrochloride mg/10 cm$^2$ | 15.00 | 14.81 |
| Tizanidine free base | 17.16 | 16.95 |
| Acrylate synthetic resin parts by weight | 50 | 50 |
| PAM Amine polymer RL parts by weight | 50 | |
| PM Amine polymer E parts by weight | | 50 |
| Polyethylene glycol 400 | 2% | 2% |
| In vitro data Active agent release mg/10 cm$^2$ | | |
| 2 hour | 14.36 | 19.48 |
| 4 hour | 15.78 | 22.22 |
| 8 hour | 17.33 | 24.03 |
| 24 hour | 22.57 | 28.98 |

EXAMPLE C

Bopindolol penetration from solutions

Solutions of the following compositions are made up and the penetration rate observed.

| Constituents | C1 | C2 | C3 |
|---|---|---|---|
| Bopindolol hydrogen malonate | — | 1.0 g | 1.0 g |
| Bopindolol (free base) | 1.0 g | — | — |
| Ethanol (ml) | 0.049 | 0.049 | 0.048 |
| Acetone (ml) | 0.049 | — | — |
| Polyethylene glycol (7) glyceryl cocoate | 0.003 | 0.003 | — |
| Water | — | — | 0.048 |
| Azone | — | — | 0.048 |
| Active agent Penetration through the rat skin (microgram/cm$^2$/hr) | | | |
| Flux | 0.8 | 0.3 | 6.0 |
| Steady state Flux | — | — | 5.8 |

What we claim is:

1. A pharmaceutical composition for the transdermal systemic administration of a pharmaceutically active agent in the form of an adhesive plaster or patch comprising a cover layer and a drug reservoir, wherein said composition comprises in a polymer matrix a homogeneous dispersion of active agent particles or a solution of active agent, said active agent being selected from the group consisting of bopindolol, tizanidine, clemastine and ketotifen, and being present in said reservoir comprising an acrylate/methacrylate polymer containing cationic ester groups.

2. A pharmaceutical composition for the transdermal systemic administration of a pharmacologically active agent in a reservoir comprising a polyacrylate polymer containing cationic ester groups, said pharmacologically active agent being selected from the group consisting of bopindolol, tizanidine, clemastine and ketotifen.

3. A composition according to claim 2 wherein the polymer is an acrylate/methacrylate polymer.

4. A composition according to any one of claims 1, 2 or 3 wherein the polymer contains trimethylaminoethyl ester groups.

5. A composition according to claim 1 in the form of an adhesive plaster or patching comprising a) a cover layer, b) a drug reservoir comprising 1 to 10 layers of a homogeneous dispersion of active agent particles or a solution of active agent in a polymer matrix, and d) an adhesive layer, reservoir c) being located between layers a) and d).

6. A composition of claim 1 comprising Bopindolol in free base form or in the form of an acid addition salt, in an acrylate/methacrylate polymer (A), containing trimethylaminoethyl ester groups, and a non-swellable acrylate resin (B), in a weight ratio of (A) to (B) of from 1:0.5 to 1:10.

7. A pharmaceutical composition according to claim 1, characterized by a skin penetration flux of at least 0.3 micrograms per $cm^2$ per hour, when measured through isolated rat skin.

8. A pharmaceutical composition according to claim 7, characterized by a skin penetration flux of at least 0.8 micrograms per $cm^2$ per hour.

* * * * *